United States Patent [19]

Yoshida et al.

[11] 4,351,922

[45] Sep. 28, 1982

[54] PROCESS FOR THE PRODUCTION OF HIGHLY WATER-ABSORBING BUT LESS WATER-SOLUBLE HYDROGELS

[75] Inventors: Tooru Yoshida, Yokohama; Seigo Iwagami, Tokyo; Takashi Ueshima; Yoshikazu Hosoda, both of Yokohama, all of Japan

[73] Assignee: Showa Denko Kabushiki Kaisha, Tokyo, Japan

[21] Appl. No.: 179,609

[22] Filed: Aug. 19, 1980

[51] Int. Cl.$^3$ .............. C08L 63/00; C08F 20/20; C08F 120/20

[52] U.S. Cl. .................. 525/116; 521/31; 521/34; 525/119; 526/287; 526/317; 526/320; 526/323.1; 526/323.2

[58] Field of Search ............... 525/116, 119; 521/31, 521/34; 526/287, 317, 320, 323.1, 323.2

[56] References Cited

U.S. PATENT DOCUMENTS

| | | |
|---|---|---|
| 3,335,112 | 8/1967 | Marks ............................ 521/34 |
| 3,501,553 | 3/1970 | Farber ........................... 525/116 |
| 3,697,467 | 10/1972 | Haughney .................... 525/119 |
| 3,751,399 | 8/1973 | Lee ............................ 526/323.1 |
| 3,850,892 | 11/1974 | Shen ............................. 526/317 |
| 3,907,737 | 9/1975 | Marx ............................ 525/119 |
| 3,947,396 | 3/1976 | Kangas ......................... 525/119 |
| 3,966,679 | 6/1976 | Gross ........................... 525/119 |
| 3,988,274 | 10/1976 | Masuhara ................... 526/323.2 |
| 4,075,148 | 2/1978 | Zatmann ..................... 525/119 |
| 4,076,921 | 2/1978 | Stol ............................. 526/317 |
| 4,268,641 | 5/1981 | Koenig ......................... 526/317 |
| 4,277,582 | 7/1981 | Mueller ........................ 526/320 |
| 4,295,762 | 10/1981 | Slovinsky .................. 526/323.1 |

*Primary Examiner*—Paul Lieberman

[57] ABSTRACT

A highly water-absorbing but less water-soluble hydrogel is produced by polymerizing at least one hydrophilic ethylenically unsaturated monomer, e.g., ethylenically unsaturated carboxylic acid, ethylenically unsaturated sulfonic acid, or derivatives thereof, in the presence of a specific difunctional compound, e.g., polyethyleneglycol diglycidyl ether, polyethyleneglycol diacrylate, etc.

20 Claims, No Drawings

PROCESS FOR THE PRODUCTION OF HIGHLY WATER-ABSORBING BUT LESS WATER-SOLUBLE HYDROGELS

BACKGROUND OF THE INVENTION

1. Field of the Invention

This invention relates to a process for production of hydrogels and more particularly to a process for producing hydrogels capable of absorbing a large amount of water which are suitable for use as water-absorbing material or as a gel material for use in a swollen state.

2. Description of the Prior Art

Nonwoven fabrics, paper, pulp, spongy urethane resins, sponges, etc. have hitherto been used as water-absorbing materials, e.g., in physiological articles, diapers, throwaway dusters, etc. These materials, however, are not necessarily satisfactory, often because of insufficient water-absorbing capabilities.

Recently, in place of such water-absorbing or water-retaining materials, materials have been proposed which are produced by crosslinking water-soluble polymeric substances with crosslinking agents or by conversion to a water-insoluble nature by replacement of part of the hydrophilic groups by lipophilic groups. For example, such materials are known to be produced by: copolymerizing acrylamide with polyfunctional compounds such as N',N'-alkylidenebisacrylamide, ethyleneglycol diacrylate and divinylbenzene (Japanese Pat. No. 23462/1968); crosslinking N-hydroxyacrylamide based polymers using light energy at low temperatures (Japanese Pat. No. 31823/1969); copolymerizing at least 50% by weight polyol methacrylate, monomers containing acidic groups, and monomers containing basic groups in the presence of polyfunctional compounds such as ethyleneglycol diacrylate, methylenebisacrylamide or divinylbenzene (Japanese Pat. No. 25749/1973); saponification of crosslinked polyethyleneglycol, crosslinked polyvinyl pyrrolidone, crosslinked sulfonated polystyrene and starch-acrylonitrile graft-copolymers (U.S. Pat. Nos. 3,661,815 and 3,669,103); preparing mixtures of saponified starch-acrylonitrile graft copolymers and soft polymers having a low glass transition temperature (Japanese Patent Application (OPI) No. 75747/1976 (The term "OPI" as used herein refers to a "published unexamined Japanese patent application")); reacting saponification products of ethylene-vinyl ester-ethylenically unsaturated carboxylic acid or derivative copolymers thereof with crosslinking agents (Japanese Patent Application (OPI) Nos. 104651/1978 and 104652/1978), copolymers of starch, cellulose or the like with acrylic acid salts or difunctional compounds (Japanese Patent Application (OPI) Nos. 130788/1978 and 130789/1978), etc.

However, when such materials are used practically, various problems occur. For example, some are insufficient in water-absorbing capability, some are complicated with respect to the production methods thereof, and when they are used in the state that they contain water therein (i.e., are in the wet state) for long periods of time, the gel structure is broken (i.e., they are thus of low stability).

SUMMARY OF THE INVENTION

As a result of extensive investigations to obtain water-absorbing materials which are free from the above-described defects of the prior art materials, it has now been found that by polymerizing hydrophilic ethylenically unsaturated monomers or monomer mixtures comprising said hydrophilic ethylenically unsaturated monomer in the presence of specific difunctional compounds, hydrogels can be relatively easily obtained, and it has further been found that these hydrogels have high water-absorbing capability and a strong gel structure, and even if used in the wet state for long periods of time they are stable.

Therefore this invention provides a process for production of highly water-absorbing but less water-soluble materials comprising polymerizing at least one hydrophilic ethylenically unsaturated monomer selected from the group consisting of a carboxylic acid containing an ethylenically unsaturated group, a sulfonic acid containing an ethylenically unsaturated group, and derivatives thereof, or a monomer mixture consisting of said hydrophilic ethylenically unsaturated monomer and another ethylenically unsaturated monomer copolymerizable therewith, in the presence of at least one difunctional compound selected from the group consisting of compounds represented by the formulae (1), (2), (3) and (4):

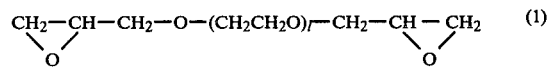

wherein l is an integer of from 5 to 100;

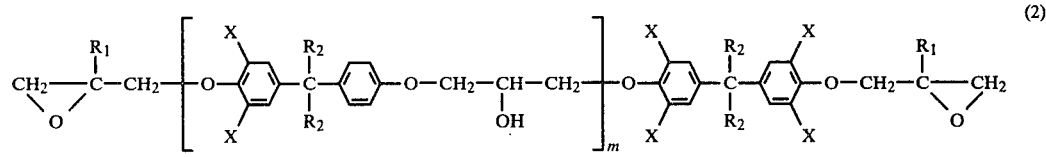

wherein $R_1$ and $R_2$, which may be the same or different, each represents hydrogen or a methyl group, X is hydrogen, a chlorine atom, or a bromine atom, and m is an integer of from 5 to 100.

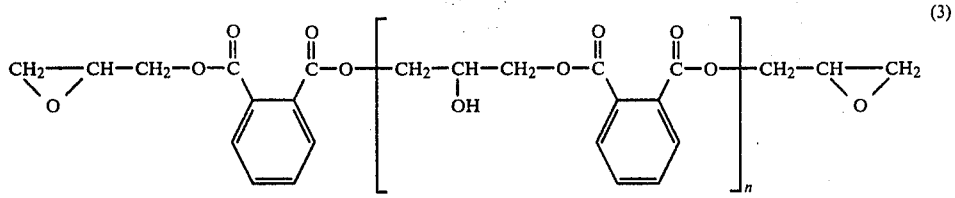

(3)

wherein n is an integer of from 5 to 100; and

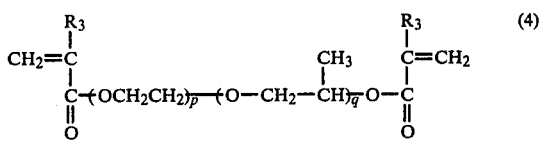

(4)

wherein $R_3$ is hydrogen or a methyl group, p is an integer of from 3 to 200, and q is 0 or an integer of from 1 to 200.

DETAILED DESCRIPTION OF THE INVENTION

In this invention, the selection and structure of the difunctional compounds (crosslinking agents) are particularly important, and more particularly the distance between two epoxy groups or acrylic or methacrylic acid groups is important. The symbols l, m and n in the general formulae (1), (2) and (3), which indicate the distance between two epoxy groups can range from 5 to 100, and preferably range from 5 to 50. The symbols p and q in the general formula (4) can range from 3 to 200 and from 0 to 200, preferably from 10 to 150 and from 0 to 150, and more preferably from 20 to 100 and from 0 to 100, respectively. The total number of p and q is preferably within the range of from 3 to 200.

Hydrogels obtained using difunctional compounds wherein l, m and n are less than 5 have only a short distance between crosslinking points, i.e., the points where the crosslinking occurs. Therefore there is no appreciable difference in the effect as a hydrogel between those hydrogels produced from such difunctional compounds and those produced from hitherto well known difunctional compounds, such as, for example, methylenebisacrylamide, ethyleneglycol diacrylate, etc. On the other hand, those hydrogels obtained using difunctional compounds wherein l, m and n are more than 100 have sufficient water-absorbing capability, but they are not desirable in that the strength of the hydrogel is low. Thus, in the production of hydrogels which are commercially useful, the selection of difunctional compounds to be used is important.

It is generally known that gel materials having water-absorbing properties can be obtained by crosslinking water-soluble polymers by use of various crosslinking agents. However, the degree of crosslinking and the water-absorbing capability are contrary to each other; that is, when the degree of cross-linking is increased to such an extent as to provide those gels which are insoluble in water, have no sticking properties in the wet state and have a desirably high strength, the water-absorbing capability often abruptly decreases, leading to the loss of usefulness as a water-absorbing material.

According to the process of this invention, however, it is possible to conveniently produce commercial hydrogels which have a sufficient distance between the crosslinking points, are subject to no marked reduction in water-absorbing capability even if the degree of crosslinking is increased, can usually absorb a very large amount of water, e.g., as much as from 10 times to several hundred times the original weight thereof, have a high gel strength in the wet state and are stable for long periods of time.

Carboxylic acids and derivatives thereof containing ethylenically unsaturated groups which can be used in this invention include carboxylic acid group-containing monomers, such as acrylic or methacrylic acid, crotonic acid, itaconic acid, maleic acid, fumaric acid, etc.; carboxylic acid base-containing monomers, such as alkali metal salts of acrylic or methacrylic acid (e.g., sodium acrylate or methacrylate, potassium acrylate or methacrylate, etc.), sodium maleate, an acrylic or methacrylic acid trimethylamine salt, an acrylic or methacrylic acid triethanolamine salt, etc.; amido group-containing monomers such as N-hexylacrylamide, acryl or methacrylamide, N-methylolated acrylamide, N,N-dimethylacrylamide, etc.; hydroxy group-containing monomers such as hydroxyethyl acrylate or methacrylate, hydroxypropyl acrylate or methacrylate, etc.; ether bond-containing monomers such as acrylic or methacrylic acid ethylene glycol monomethyl ether, acrylic or methacrylic acid trioxyethylene glycol, etc.; amino group-containing monomers such as dimethylaminoethyl acrylate or methacrylate, diethylaminoethyl acrylate or methacrylate, etc.; quaternary ammonium base-containing monomers such as N,N,N-trimethyl-N-acryloyl (or methacrylolyl)oxyethyl ammoniumchloride, N,N,N-triethyl-N-acryloyl (or methacryloyl)oxyethyl ammoniumchloride, and so forth.

Sulfonic acids and derivatives thereof containing ethylenically unsaturated group which can be used in this invention include sulfonic acid group-containing monomers, such as vinylsulfonic acid, vinyltoluenesulfonic acid, styrenesulfonic acid, sulfopropyl acrylate or methacrylate, etc., and sulfonic acid salt-containing monomers such as sodium vinylsulfonate, a vinylsulfonic acid methylamine salt, sodium sulfopropyl acrylate or methacrylate, an acrylic or methacrylic acid sulfopropyldiethanolamine salt, sodium styrenesulfonate, etc.

Of these compounds, carboxylic acid base-containing monomers, amido group-containing monomers and sodium styrenesulfonate are preferred, and alkali metal salts of acrylic or methacrylic acid are particularly preferred when the difunctional compound represented by the formula (1), (2) or (3) is used.

These carboxylic acids and sulfonic acids and derivatives thereof containing ethylenically unsaturated groups can be used alone or in combination with each other.

Ethylenically unsaturated monomers which are copolymerizable with the above difunctional compounds, with carboxylic acids containing ethylenically unsaturated groups, and with sulfonic acids containing ethylenically unsaturated groups and derivatives thereof include ester bond-containing monomers such as methyl acrylate or methacrylate, ethyl acrylate or methacrylate, dimethylaminoethyl acrylate or methacrylate, vinyl acetate, etc.; nitrile group-containing monomers such as acrylonitrile or methacrylonitrile, etc.; styrene-based monomers such as styrene, α-methylstyrene, o-methylstyrene, p-methylstyrene, p-aminostyrene, o-aminostyrene, etc.; vinyl pyridine based monomers such as 2-vinyl pyridine, 3-vinyl pyridine, etc., and the like.

These ethylenically unsaturated monomers which can be used as a copolymerization component may be used singly or in combination with each other. While the amount of the copolymerization component added is not limited so long as the resulting copolymer is hydrophilic, it is preferably 50% by weight or less based upon the total weight of all monomers.

Examples of difunctional compounds represented by formulae (1), (2), (3) and (4) are given below.

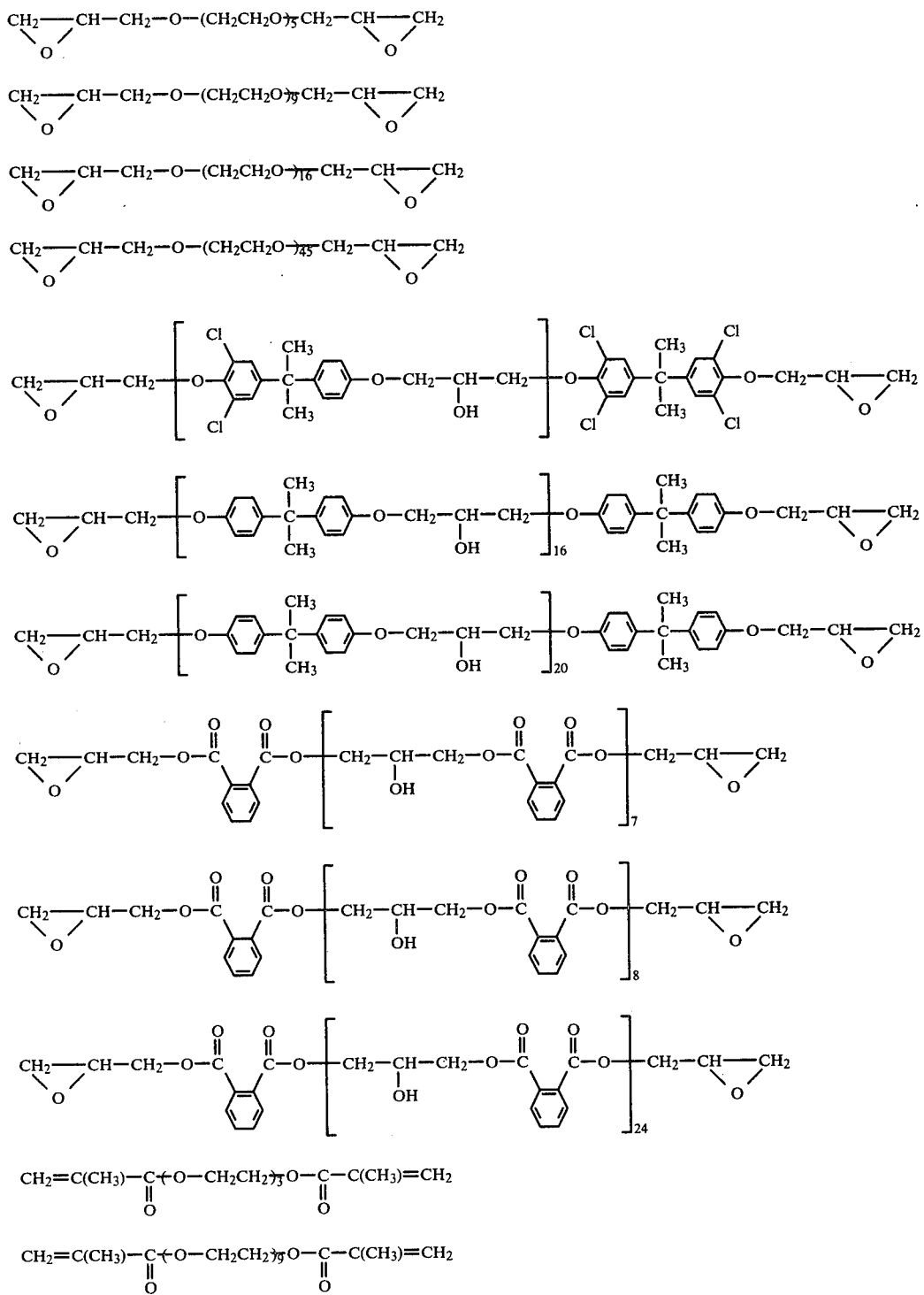

-continued

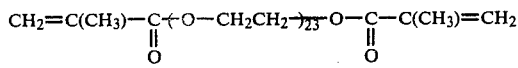

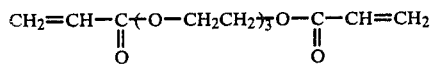

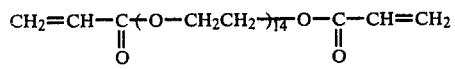

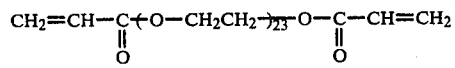

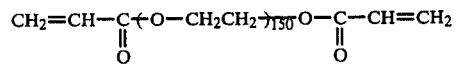

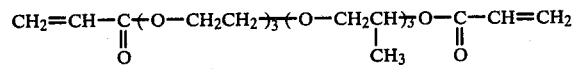

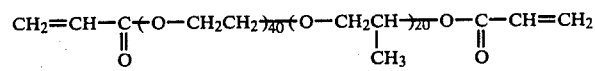

Difunctional compounds represented by the formula (1), (2) and (3) can easily be produced by the dehydrochlorination reaction of epichlorohydrin with a bisphenol having a structure corresponding to the repeating unit in the formulae (1), (2) and (3). These difunctional compounds are also available as a commercial product, for example, Shodyme 810, Shodyme 520 (produced by Showa Denko K. K.), etc. Difunctional compounds represented by the formula (4) can also be produced with ease by reacting, for example, acrylic or methacrylic acid chloride and polyoxyalkyleneglycol in the presence of a dehydrochlorination agent. The polyoxyalkyleneglycol as used herein can be obtained by polymerizing ethyleneoxide or copolymerizing ethyleneoxide and propyleneoxide in the presence of, for example, alkyleneglycol. The values of p and q can be suitably controlled by changing the molar ratio of alkyleneglycol to ethyleneoxide, or alkyleneglycol to ethyleneoxide to propyleneoxide.

Difunctional compounds represented by the above formulae (1), (2), (3) and (4) may be used alone or in admixtures comprising two or more thereof. While the amount of the difunctional compound used is not critical, it is generally from about 0.005% to 20% by weight, preferably from 0.01% to 5% by weight, and more preferably from 0.01% to 1% by weight based upon the total weight of the ethylenically unsaturated monomers.

When the amount of the difunctional compound used is 0.005% by weight or less, the formed hydrogel has high water-absorbing capability, but the swollen gel thereof becomes increasingly sticky, which is generally not desirable. On the other hand, when the amount of the difunctional compound being used is 20% by weight or more, the water-absorbing capability may be undesirably lowered or unreacted difunctional compounds may undesirably remain.

Any hitherto known methods can be used for polymerizing the ethylenically unsaturated monomer or a monomer mixture consisting of the ethylenically unsaturated monomer and another ethylenically unsaturated monomer copolymerizable therewith in the presence of the difunctional compound. For example, methods can be used in which the polymerization is carried out in a polymerization solvent, e.g., water, methanol, ethanol, tetrahydrofuran, acetone or a mixture thereof in the presence of a radical polymerization catalyst, e.g., a cerium (IV) salt, hydrogen peroxide, benzoyl peroxide, azobisisobutylonitrile, ammonium persulfate, etc., and in which the polymerization is carried out by use of a so-called redox catalyst prepared by combining a persulfuric acid salt, e.g., potassium persulfate, ammonium persulfate, etc. and an organic amine, e.g., aniline, monoethanolamine, hexamethylenediamine, diethanolamine, dimethylaniline, triethanolamine, tetramethylethylenediamine, etc..

In some cases, a so-called water-in-oil type suspension polymerization method in which an aqueous solution is suspended in an organic solvent can be employed.

The amount of the radical polymerization catalyst used is typically from 10 to 3,000 ppm, and preferably 100 to 1,500 ppm, based upon the total weight of the ethylenically unsaturated monomers.

While the polymerization temperature can be varied depending upon the type of the catalyst used, it is usually from 10° C. to 150° C., and preferably from 20° C. to 100° C. The polymerization time is typically from 1 hour to 9 hours. While the reaction may be carried out either in air or in the atmosphere of nitrogen gas, it is preferred to carry out in the atmosphere of nitrogen gas.

The reaction product can be converted into a powder form by application of a precipitation treatment using non-solvents such as methanol, acetone and the like, and be evaporation treatment can be supplied in a dry powder form.

Hydrogels of this invention obtained by the above described method can be used not only as a sole material in which water is merely to be absorbed, but can also be used in combination with paper, fibers, cloth or other materials as various sanitary materials which come in contact with human body, such as throwaway diapers, tampons, sanitary cotton, bandages, napkins, etc. Furthermore, since they scarcely degenerate even if used in the wet state for long periods of time, they can suitably be used in various industrial applications, for example, as an agent for separating water in oil, as a dehydrating agent, as a drying agent, as a carrier for chromatography, as a water retaining agent for plants or soil, and the like. Additionally they find applications in those fields wherein water-absorbing or water-retaining properties are utilized. Moreover, hydrogels of this invention can easily be produced on a commercial scale, and spherical hydrogels can be used as a carrier material.

Coloring agents, perfume, fillers and other additives can be added to hydrogels of this invention in amounts which do not lead to deterioration of the properties of the hydrogels.

Hereinafter this invention will be explained in greater detail by reference to the examples and comparative examples.

The water absorption amount and water absorption ratio in Examples 1 to 9 and 24 to 30 and Comparative Examples 1 to 3 were measured according to the following method:

0.5 g of a sample was soaked in 500 ml of water and allowed to stand therein for 2 hours. By application of suction-filtration by use of a glass fiber, surplus water was removed, and the total weight of the glass filter and the water-containing sample was measured.

Water Absorption Amount (g) = (Total Weight) − (Weight of Glass Filter) − 0.5

Water Absorption Ratio (%) = $\frac{\text{Water Absorption Amount}}{0.5} \times 100$ The water absorption amount and water absorption ratio in Examples 10 to 23 and Comparative Examples 4 to 10 were measured in the same manner as above, except that 0.5 g of a sample was soaked in 100 ml of water.

EXAMPLES 1 TO 5 AND COMPARATIVE EXAMPLES 1 TO 2

10 g of acrylic acid, 30 g of ion exchanged water and 21.8 ml of a 7 N aqueous solution of sodium hydroxide were added to a reactor equipped with a stirrer, a nitrogen introduction conduit and a thermometer, and the solution was adjusted to a pH of 10.2. The concentration of monomer in the aqueous phase was 16% by weight.

Polyethyleneglycol diglycidyl ether (hereinafter referred to merely as "PEGE") represented by the following formula:

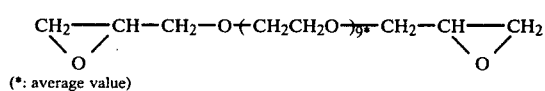
(*: average value)

was introduced into the reactor as a difunctional compound in the proportion as illustrated in Table 1, and vacuum-deairing and nigrogen-replacement (that is, replacement of air by nitrogen) were carried at ordinary temperature for 5 to 10 minutes and 1 hour, respectively. Thereafter, 0.25 ml of a 1% aqueous solution of ammonium persulfate (250 ppm based on acrylic acid) and 0.25 ml of a 6% aqueous solution of triethanolamine (1,500 ppm based on acrylic acid) were added to the reactor, and they were reacted with stirring at 70° C. for 4 hours.

After the reaction was completed, the reaction product was washed with a mixed solution of water and methanol, dried under reduced pressure at 50° C. for about 24 hours, and pulverized to thereby obtain dry gel powder. The water absorption amount and water absorption ratio of the so obtained gel were measured and are shown in Table 1.

For comparison, a gel was produced in the same manner as above, except that methylenebisacrylamide (hereinafter referred to merely as "MBAA") was used in place of PEGE. The water absorption amount and water absorption ratio of the gel obtained were measured and are shown in Table 1.

TABLE 1

|  | Difunctional Compound | | Yield (%) | Water Absorption Properties | |
|---|---|---|---|---|---|
|  | PEGE (g) | MBAA (g) |  | Water Absorption Amount (g) | Water Absorption Ratio (wt %) |
| Example |  |  |  |  |  |
| 1 | 0.05 | — | 99.6 | 82.700 | 16540 |
| 2 | 0.1 | — | 98.2 | 58.810 | 11762 |
| 3 | 0.2 | — | 98.3 | 53.000 | 10600 |
| 4 | 0.4 | — | 97.6 | 44.350 | 8870 |
| 5 | 0.8 | — | 99.5 | 31.250 | 6250 |
| Comparative Example |  |  |  |  |  |
| 1 | — | 0.1 | 99.5 | 36.575 | 7315 |
| 2 | — | 0.8 | 100.1 | 6.800 | 1360 |

EXAMPLE 6

A gel was produced in the same manner as in Example 4 except that the same amount by weight of methacrylic acid was used in place of acrylic acid.

The water absorption amount and water absorption ratio of the above obtained dry powdery gel were 40.25 g and 8050% by weight, respectively.

EXAMPLE 7

A gel was produced in the same manner as in Example 2 except that a compound represented by the formula

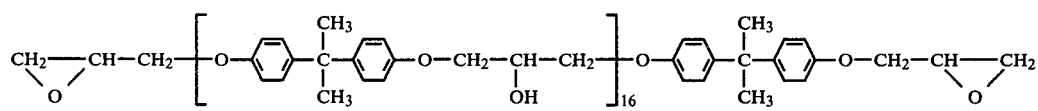

was used in place of PEGE, and the reaction temperature was changed to 40° C. The yield was 98.7%. The water absorption amount of the dry powdery gel obtained was 90.1374 g, and the water absorption ratio was 18027% by weight.

EXAMPLE 8

A gel was produced in the same manner as in Example 2 except that a compound represented by the formula

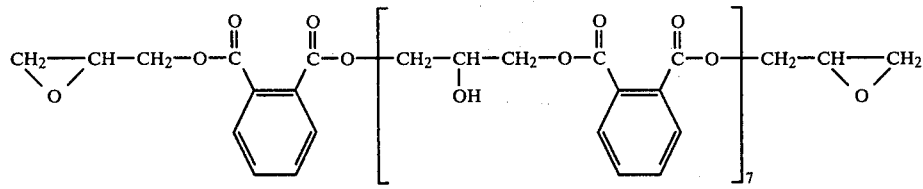

was used in place of PEGE, and the reaction temperature was changed to 40° C. The yield was 99.3%. The water absorption amount of the dry powder obtained was 75 g, and the water absorption ratio was 15000% by weight.

EXAMPLE 9

To the same reactor as used in Examples 1 to 5, 10 g of acrylic acid, 30 g of ion exchanged water and 21.8 ml of a 7 N aqueous solution of sodium hydroxide were added, and the solution was adjusted to pH 10.2.

Thereafter, 4 g of acrylonitrile, as a copolymerization component, and 0.1 g of PEGE, as used in Examples 1 to 5, were added to the reactor, and vacuum-deairing and nitrogen-replacement were carried out at ordinary temperature for 5 to 10 minutes and 1 hour, respectively. Then, 0.30 ml of a 1% aqueous solution of ammonium persulfate (250 ppm based on the total weight of acrylic acid and acrylonitrile) and 0.30 ml of a 6% aqueous solution of triethanolamine (1,500 ppm based on the total weight of acrylonitrile and acrylic acid) were added to the reactor. Thereinafter, in the same manner as in Examples 1 to 5, polymerization and post-treatment were carried out. The yield was 97.7%.

The water absorption amount and water absorption ratio were measured for the reaction product obtained and found to be 46.2150 g and 9243% by weight, respectively. Copolymerization of acrylonitrile slightly lowers the water absorption amount and water absorption ratio as compared with those in Example 2, but it provided flexibility to the formed gel.

COMPARATIVE EXAMPLE 3

A gel was produced in the same manner as in Example 9, except that methylenebisacrylamide was used in place of PEGE.

The water absorption amount of the dry powder obtained was 7.8930 g and the water absorption ratio was 1578% by weight.

EXAMPLES 10 TO 13 AND COMPARATIVE EXAMPLES 4 TO 7

To a reactor equipped with stirrer, a nitrogen introduction conduit, and a thermometer, there was added 20 g of a 50% aqueous solution of acrylamide, 40 g of ion exchanged water, and amounts as indicated in Table 2 of polyethyleneglycol diacrylate (PEGDA) represented by the formula

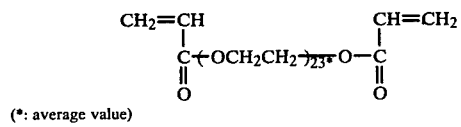

(*: average value)

Then vacuum-deairing and nitrogen-replacement were carried out at ordinary temperature for 5 to 10 minutes and 1 hour, respectively.

Thereafter, 0.25 ml of a 1% aqueous solution of ammonium persulfate (250 ppm based on acrylamide) and 0.25 ml of a 6% aqueous solution of triethanolamine (1,500 ppm based on acrylamide) were added to the reactor, and were polymerized with stirring at 40° C. for 4 hours.

After the reaction was completed, the reaction product was washed with a mixed solution of water and methanol, dried under reduced pressure at 50° C. for about 24 hours, and pulverized, to thereby obtain a dry gel powder. The water absorption amount and water absorption ratio of the above-obtained gel are shown in Table 2.

For comparison, a gel was produced in the same manner as above except that methylenebisacrylamide (MBAA) was used in place of polyethyleneglycol diacrylate (PEGDA).

TABLE 2

| | Difunctional Compound | | Yield (%) | Water Absorption Properties | |
|---|---|---|---|---|---|
| | PEGDA (g) | MBAA (g) | | Water Absorption Amount (g) | Water Absorption Ratio (% by weight) |
| Example | | | | | |
| 10 | 0.05 | — | 98.7 | 6.3707 | 1274 |
| 11 | 0.1 | — | 100.3 | 5.8437 | 1169 |
| 12 | 0.2 | — | 99.6 | 5.9461 | 1189 |
| 13 | 0.4 | — | 97.2 | 5.8679 | 1174 |
| Comparative Example | | | | | |
| 4 | — | 0.05 | 99.5 | 4.3899 | 877 |
| 5 | — | 0.1 | 98.9 | 4.4322 | 886 |
| 6 | — | 0.2 | 99.1 | 3.5690 | 713 |
| 7 | — | 0.4 | 98.7 | 3.0185 | 603 |

EXAMPLES 14 TO 18 AND COMPARATIVE EXAMPLES 8 AND 9

To a reactor equipped with a stirrer, a nitrogen introduction conduit, and a thermometer there was added 10 g of acrylic acid, 30 g of ion exchanged water and 21.8 ml of a 7 N aqueous solution of sodium hydroxide, and the solution was adjusted to a pH of 10.2.

Thereafter, polyethyleneglycol diacrylate (PEGDA) as used in Examples 10 to 13 was added to the reactor in the proportion as illustrated in Table 3, and vacuum-deairing and nitrogen-replacement were carried out at ordinary temperature for 5 to 10 minutes and 1 hour, respectively. Then, 0.25 ml of a 1% aqueous solution of ammonium persulfate (250 ppm based on acrylic acid) and 0.25 ml of a 6% aqueous solution of triethanolamine (1,500 ppm based on acrylic acid) were added to the reactor, and were polymerized with stirring at 40° C. for 4 hours.

Thereinafter, the same procedure as above was applied to obtain a dry gel, and the water absorption amount and water absorption ratio were measured and are shown in Table 3.

For comparison, a gel was produced in the same manner as above, except that methylenebisacrylamide (MBAA) was used in place of polyethyleneglycol diacrylate (PEGDA), and the gel was tested in the same manner as above.

TABLE 3

| | Difunctional Compound | | | Water Absorption Properties | |
|---|---|---|---|---|---|
| | PEGDA (g) | MBAA (g) | Yield (%) | Water Absorption Amount (g) | Water Absorption Ratio (% by weight) |
| Example | | | | | |
| 14 | 0.02 | — | 99.2 | 139.2500 | 27850 |
| 15 | 0.05 | — | 99.3 | 97.2254 | 19445 |
| 16 | 0.1 | — | 100 | 69.9775 | 13995 |
| 17 | 0.2 | —. | 99.4 | 57.9500 | 11590 |
| 18 | 0.4 | — | 98.9 | 48.8250 | 9765 |
| Comparative Example | | | | | |
| 8 | — | 0.1 | 99.5 | 36.5750 | 7315 |
| 9 | — | 0.4 | 100.2 | 22.2216 | 4444 |

EXAMPLE 19

To a reactor equipped with a stirrer, a nitrogen introduction conduit, and a thermometer there was added 10 g of acrylic acid, 30 g of ion exchanged water and 21.8 ml of a 7 N aqueous solution of sodium hydroxide, and the solution was adjusted to pH of 10.2.

Then, 0.1 g of poly(ethylene-propylene)glycol diacrylate having the formula

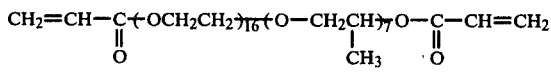

was added to the reactor, and vacuum-deairing and nitrogen-replacement were carried out at ordinary temperature for 5 to 10 minutes and 1 hour, respectively. Thereafter, 0.25 ml of a 1% aqueous solution of ammonium persulfate and 0.25 ml of a 6% aqueous solution of triethanolamine were added to the reactor, and were polymerized with stirring at 40° C. for 4 hours. The yield was 99.7%.

The reaction product was dried, and the water absorption amount and water absorption ratio were measured and found to be 48.9842 g and 9796% by weight, respectively.

EXAMPLE 20

A gel was produced in the same manner as in Example 19, except that 0.1 g of polyethyleneglycol diacrylate represented by the formula

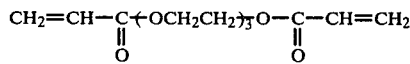

was used instead of the poly(ethylene-propylene)glycol diacrylate. The yield was 98.5%.

The reaction product obtained was dried, and the water absorption amount and water absorption ratio were measured and found to be 62.9797 g and 12595% by weight, respectively.

EXAMPLE 21

A gel was produced in the same manner as in Example 19, except that 0.1 g of polyethyleneglycol diacrylate represented by the formula

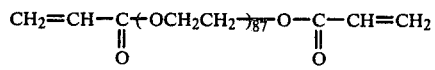

was used instead of the poly(ethylene-propylene)glycol diacrylate. The yield was 100%.

The reaction product was dried, and the water absorption amount and water absorption ratio were measured and found to be 76.9752 g and 15395% by weight, respectively.

EXAMPLE 22

In a reactor equipped with a stirrer, a nitrogen introduction conduit and a thermometer were placed 20 g of a 50% aqueous solution of hydroxymethylacrylamide, 40 g of ion exchanged water and 0.05 g of polyethyleneglycol diacrylate as used in Examples 10 to 13. They were polymerized and subjected to post-treatment in the same manner as in Examples 10 to 13. The yield was 99.2%.

The reaction product was dried, and the water absorption amount and water absorption ratio were measured and found to be 11.16 g and 2232% by weight, respectively.

COMPARATIVE EXAMPLE 10

A gel was produced in the same manner as in Example 22 except that methylenebisacrylamide was used in place of the polyethyleneglycol diacrylate. The yield was 98.2%.

The water absorption amount and water absorption ratio were 6.875 g and 1375% by weight, respectively.

EXAMPLE 23

To the same reactor as used in Examples 14 to 18, there was added 10 g of acrylic acid, 30 g of ion exchanged water and 21.8 ml of a 7 N aqueous solution of sodium hydroxide, and the solution was adjusted to pH of 10.2.

Then, 2.0 g of acrylonitrile and 0.05 g of polyethyleneglycol diacrylate as used in Examples 14 to 18 were added to the reactor, and vacuum-deairing and nitrogen-replacement were carried out at room temperature for 5 to 10 minutes and 1 hour, respectively.

Thereafter, 0.30 ml of a 1% aqueous solution of ammonium persulfate and 0.30 ml of a 6% aqueous solution of triethanolamine were added to the reactor, and they were polymerized and subjected to post-treatment in the same manner as in Examples 14 to 18. The yield was 97.8%.

The water absorption amount and water absorption ratio were measured and found to be 86.57 g and 17314% by weight, respectively. Copolymerization of acrylonitrile slightly lowered the water absorption amount and water absorption ratio as compared with those in Example 15, but it provided improved flexibility to the gel.

EXAMPLE 24

A gel was produced in the same manner as in Example 1, except that the same amount by weight of styrenesulfonic acid was used in place of acrylic acid.

The water absorption amount and water absorption ratio of the thus obtained powdery gel were 45 g and 9000% by weight, respectively.

EXAMPLE 25

A gel was produced in the same manner as in Example 7, except that the same amount by weight of styrenesulfonic acid was used in place of acrylic acid.

The water absorption amount and water absorption ratio of the thus obtained powdery gel were 85 g and 17000% by weight, respectively.

EXAMPLE 26

A gel was produced in the same manner as in Example 8, except that the same amount by weight of styrenesulfonic acid was used in place of acrylic acid.

The water absorption amount and water absorption ratio of the thus obtained powdery gel were 32 g and 6400% by weight, respectively.

EXAMPLE 27

A gel was produced in the same manner as in Example 10, except that 10 g of styrenesulfonic acid and 0.25 ml of a 3% aqueous solution of sodium sulfite were used in place of 20 g of a 50% aqueous solution of acrylamide and 0.25 ml of a 6% aqueous solution of triethanolamine, respectively.

The water absorption amount and water absorption ratio of the thus obtained powdery gel were 50 g and 10000% by weight, respectively.

EXAMPLE 28

A gel was produced in the same manner as in Example 19, except that the same amount by weight of styrenesulfonic acid was used in place of acrylic acid.

The water absorption amount and water absorption ratio of the thus obtained powdery gel were 47 g and 9400% by weight, respectively.

EXAMPLE 29

A gel was produced in the same manner as in Example 1, except that 10 g of acrylic acid and 50 g of ion exchanged water were added to a reactor with no addition of a 7 N aqueous solution of sodium hydroxide.

The water absorption ratio of the thus obtained powdery gel was 9000% by weight.

EXAMPLE 30

A gel was produced in the same manner as in Example 10, except that 10 g of acrylic acid was used in place of acrylamide.

The water absorption ratio of the thus obtained powdery gel was 7300% by weight.

While the invention has been described in detail and with reference to specific embodiments thereof, it will be apparent to one skilled in the art that various changes and modifications can be made therein without departing from the spirit and scope thereof.

What is claimed is:

1. A process for producing a highly water-absorbing but less water-soluble hydrogel comprising polymerizing at least one hydrophilic ethylenically unsaturated monomer selected from the group consisting of a carboxylic acid containing an ethylenically unsaturated group, a sulfonic acid containing an ethylenically unsaturated group, and derivatives thereof to form a homopolymer or copolymer of said hydrophilic ethylenically unsaturated monomer, or a mixture of at least 50% of said hydrophilic ethylenically unsaturated monomer and less than 50% of an ethylenically unsaturated monomer copolymerizable therewith other than said hydrophilic ethylenically unsaturated monomer, in the presence of 0.005% to 20% by weight based on the total weight of the ethylenically unsaturated monomers of at least one difunctional compound selected from the group consisting of compounds represented by the formula (1):

$$CH_2-CH-CH_2-O-(CH_2CH_2O)_l-CH_2-CH-CH_2 \quad (1)$$
$$\diagdown O \diagup \qquad\qquad\qquad\qquad\qquad \diagdown O \diagup$$

wherein $l$ is an integer of from 5 to 100.

2. A process for producing a highly water-absorbing but less water-soluble hydrogel comprising polymerizing at least one hydrophilic ethylenically unsaturated monomer selected from the group consisting of a carboxylic acid containing an ethylenically unsaturated group, a sulfonic acid containing an ethylenically unsaturated group, and their derivatives selected from a carboxylic acid base-containing monomer, an amido-group containing monomer or sodium styrenesulfonate to form a honopolymer or copolymer of said hydrophilic ethylenically unsaturated monomers, or a mixture of at least 50% of said hydrophilic ethylenically unsaturated monomer and less than 50% of ethylenically unsaturated monomer copolymerizable therewith other than said hydrophilic ethylenically unsaturated monomer, in the presence of 0.005% to 20% by weight based on the total weight of the ethylenically unsaturated monomers of at least one difunctional compound represented by formula (4):

$$\begin{matrix} R_3 & & & & R_3 \\ | & & & & | \\ CH_2=C & & CH_3 & & C=CH_2 \\ | & & | & & | \\ C-(OCH_2CH_2)_p-(O-CH_2-CH)_q-O-C \\ \| & & & & \| \\ O & & & & O \end{matrix} \quad (4)$$

wherein $R_3$ is hydrogen or a methyl group, p is an integer of from 10 to 150, and q is 0 or an integer of from 1 to 150.

3. A process as in claim 2, wherein said carboxylic acid base-containing monomer is an alkali metal salt of acrylic or methacrylic acid, sodium maleate, an acrylic or methacrylic acid trimethylamine salt or an acrylic or methacrylic acid triethanolamine salt, and said amido group containing monomer is N-hexylacrylamide, acryl or methacrylamide, N-methylolated acrylamide or N,N-dimethylacrylamide.

4. A process as in claim 2, wherein said hydrophilic ethylenically unsaturated monomer is selected from the group consisting of a sulfonic acid containing an ethylenically unsaturated group and sodium styrenesulfonate.

5. A process as in claim 4, wherein said sulfonic acid containing an ethylenically unsaturated group is selected from the group consisting of vinylsulfonic acid, vinyltoluenesulfonic acid, styrenesulfonic acid and sulfopropyl acrylate or methacrylate.

6. A water-absorbing but less water-soluble hydrogel produced by a process as in claim 1, 2, 3, 4 or 5.

7. A process as in claim 1, wherein the materials polymerized consist essentially of said at least one hydrophilic ethylenically unsaturated monomer and said at least one difunctional compound.

8. A process as in claim 2, wherein the materials polymerized consist essentially of said at least one hydrophilic ethylenically unsaturated monomer and said at least one difunctional compound.

9. A process as in claim 1 or 2 wherein the carboxylic acid containing an ethylenically unsaturated group is selected from the group consisting of acrylic or methacrylic acid, crotonic acid, itaconic acid, maleic acid and fumaric acid.

10. A process as in claim 1 or 2 wherein the sulfonic acid containing an ethylenically unsaturated group is selected from the group consisting of vinylsulfonic acid, vinyltoluenesulfonic acid, styrenesulfonic acid and sulfopropyl acrylate or methacrylate.

11. A process as in claim 1 or 2 wherein the derivative of the carboxylic acid containing an ethylenically unsaturated group is a carboxylic acid base-containing monomer, or an amido group-containing monomer and the derivative of the sulfonic acid containing an ethylenically unsaturated group is sodium styrenesulfonate.

12. A process as in claim 1 or 2 wherein said difunctional said hydrophilic ethylenically unsaturated monomer is an alkali metal salt of acrylic or methacrylic acid. said hydrophilic ethylenically unsaturated monomer is an alkali metal salt of acrylic or methacrylic acid.

13. A process as in claim 1 or 2 wherein the ethylenically unsaturated monomer copolymerizable with the hydrophilic ethylenically unsaturated monomer is selected from the group consisting of ester bond-containing monomers, nitrile group-containing monomers, styrene-based monomers, and vinyl pyridine-based monomers.

14. A process as in claim 1 or 2 wherein the amount of the difunctional compound added is from 0.01% to 5% by weight, based upon the total weight of the ethylenically unsaturated monomers.

15. A process as in claim 1 or 2 wherein the amount of the difunctional compound added is from 0.01% to 1% by weight, based upon the total weight of the ethylenically unsaturated monomers.

16. A process as in claim 1 or 2 wherein the polymerization is carried out at a temperature of from about 10° C. to 150° C. for a period of from about 1 to 9 hours.

17. A process as in claim 1 or 2 wherein l is an integer of from 5 to 50.

18. A process as in claim 16, wherein said temperature is from 20° C. to 100° C.

19. A process as in claim 1 or 2, wherein said difunctional compound is a compound represented by the formula (4).

20. A process as in claim 1 or 2, wherein the materials polymerized consist essentially of said at least one hydrophilic ethylenically unsaturated monomer and said at least one difunctional compound.

* * * * *